United States Patent [19]

Flower

[11] Patent Number: 5,645,526
[45] Date of Patent: Jul. 8, 1997

[54] APPARATUS AND METHOD FOR ENSURING COMPATIBILITY OF A REUSABLE IONTOPHORETIC CONTROLLER WITH AN IONTOPHORETIC PATCH

[75] Inventor: Ronald J. Flower, Vernon, N.J.

[73] Assignee: Becton Dickinson and Company, Franklin Lakes, N.J.

[21] Appl. No.: 315,372

[22] Filed: Sep. 30, 1994

[51] Int. Cl.[6] ................................... A61N 1/30
[52] U.S. Cl. ............................ 604/20; 607/115
[58] Field of Search ................ 604/20–21, 890.1, 604/290; 607/149–153, 52, 51, 115, 63; 128/908

[56] References Cited

U.S. PATENT DOCUMENTS

| | | | |
|---|---|---|---|
| 4,141,359 | 2/1979 | Jacobsen et al. | 607/63 |
| 4,808,152 | 2/1989 | Sibalis | 604/20 |
| 4,931,046 | 6/1990 | Newman . | |
| 4,942,883 | 7/1990 | Newman . | |
| 5,224,928 | 7/1993 | Sibalis et al. | 604/20 |

FOREIGN PATENT DOCUMENTS

| | | | |
|---|---|---|---|
| 0652135 | 6/1991 | Australia | 604/20 |

*Primary Examiner*—Mark Bockelman
*Attorney, Agent, or Firm*—Allen W. Wark, Esq.

[57] ABSTRACT

An iontophoretic drug delivery device including a reusable controller and patch are disclosed. The controller and patch include electronics which ensure compatibility of the reusable iontophoretic controller with the specific patch to which it is connected. If the controller determines that the patch is incompatible with the controller, the controller does not apply current to the patch.

17 Claims, 4 Drawing Sheets

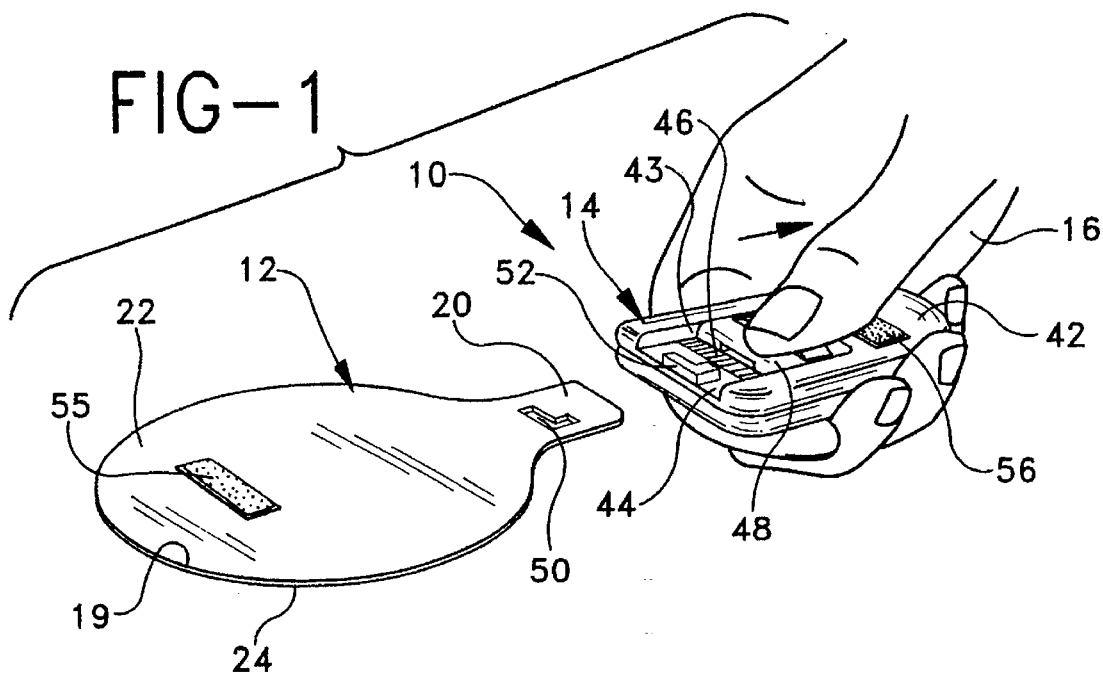
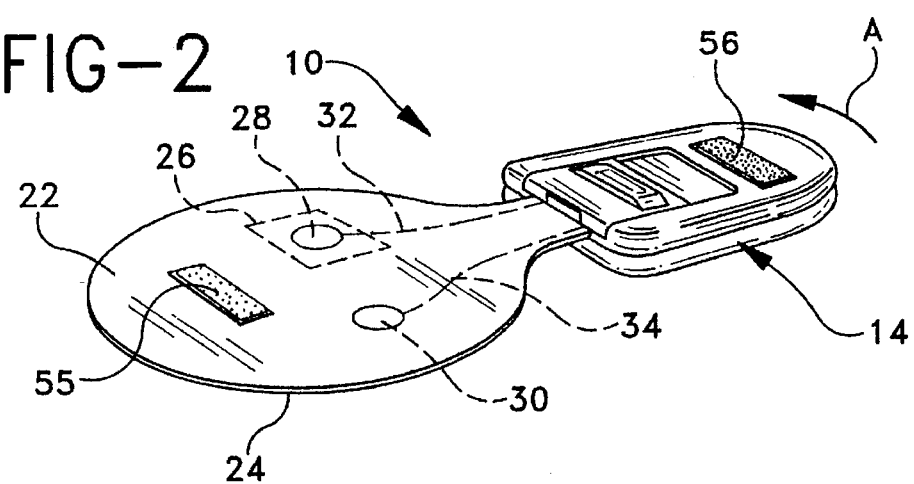
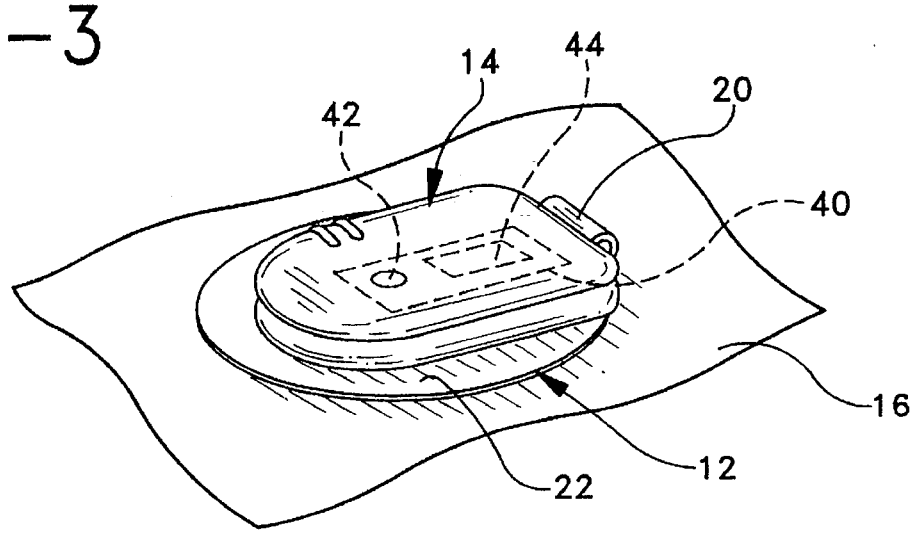

5,645,526

APPARATUS AND METHOD FOR ENSURING COMPATIBILITY OF A REUSABLE IONTOPHORETIC CONTROLLER WITH AN IONTOPHORETIC PATCH

BACKGROUND OF THE INVENTION

1. Field of the Invention

The present invention relates to controllers and patches for iontophoretic devices, and more particularly relates to ensuring compatibility of a reusable iontophoretic controller with an appropriate iontophoretic patch.

2. Description of the Prior Art

Iontophoresis can be defined as the introduction, by means of an electric current, of ions of soluble salts into the tissues of the body for therapeutic purposes. Iontophoretic devices have, in recent years, become an increasingly important means of administering therapeutic agents. Such systems offer advantages clearly not achievable by any other methods of drug administration requiring ingestion, or injection through the skin.

A recent development in iontophoretic devices is the use of a separate, reusable controller which is removably, electrically coupled to a patch containing the therapeutic agent or drug. The reusable controller includes a power source, such as a battery, and electronics which can control the amount of current applied to the patch as well as the amount of time current is to be applied. Such a device is described in U.S. Pat. No. 4,942,883. The iontophoretic device includes a power supply source and a microprocessor control system. The housing of the power supply source and microprocessor is arranged so that a carrier or patch containing a drug to be delivered to a patient can be attached to an open underside of the housing. The '883 patent teaches that the dosage rate (drug delivery time) and other required parameters for the known dosage to be administered by a certain patch are entered into the microprocessor control system by the user through the use of programmable pads or by a card or tape containing such information. A concern with this type of arrangement, a two component system having a reusable controller, is that the controller may be inadvertently used with an incompatible patch.

More specifically, if an error is made in programming the dosage rate or other dosage parameters, a patient may be severely harmed. For example, the patient may be burned by excessive current being applied to the patch or the patient may be harmed by an excessive amount of drug being driven into the patient's body. Alternatively, if not enough drug is being delivered to the patient, the patient's condition may worsen. The prior art provides no safety measures to ensure that a reusable controller is utilized with a compatible patch to provide proper drug dosages and time periods of dosages. Therefore, there is a need for a system of verifying that compatible controllers and patches are used when administering drugs transdermally with reusable controllers.

Yet another factor in the design of iontophoretic devices is to make the device cost efficient. In order for iontophoretic devices to be cost effective and competitive with conventional forms of therapy such as pills and subcutaneous injections, the cost of each component and feature must be kept to a minimum while ensuring the safety and health of the patient using the device. Accordingly, there is a need to keep the cost of the safety measures low while ensuring proper administration of a medicament.

It is therefore an object of the present invention to provide an iontophoretic device having a reusable controller which includes means to ensure that the patch and controller are compatible prior to any medicament being transdermally administered.

It is another object of the present invention to provide a cost efficient iontophoretic device having proper safety measures to ensure compatibility of the controller with the medicament containing patch.

SUMMARY OF THE INVENTION

In accordance with one form of the present invention, an iontophoretic device includes a controller for providing a specific current to the iontophoretic device. The device includes a patch for attaching to the skin of a patient for transdermally delivering medicament through the skin. The iontophoretic device includes means for electrically matching the controller to the patch. In this manner, the iontophoretic device prevents current from the controller from being applied to the patch if the controller and patch are determined to be incompatible.

In order to determine if the controller and patch are compatible, the iontophoretic device includes electronic means located on either the patch, the controller or both, which enables the controller to determine its compatibility with the patch. More specifically, in one embodiment of the present invention, both the patch and controller include a resistive network, which based upon the ratios of the resistances of the controller and patch network circuits, the controller can determine compatibility with the patch to which it is connected. Compatibility of the patch and controller is defined as the controller providing a proper dosage rate (a specific current over a specified period of time) for the medicament to be transdermally driven from the patch into the patient's body. Accordingly, if the controller and patch are deemed by the controller to be incompatible, the controller will not permit current to flow to the patch. Thus, the system ensures the safety of the user, by only permitting compatible controllers and patches to be utilized by the patient.

In one embodiment of the present invention, the controller includes a microprocessor to determine compatibility of the controller with the patch. The microprocessor can be preprogrammed to deliver the correct dosage rate for a specific drug or therapeutic agent to be iontophoretically delivered to the patient. Alternatively, by identifying a patch, the controller can program itself to deliver the correct dosage.

In an alternative embodiment, the safety measure for compatibility of the controller with the patch includes a serial number located on the patch and the controller including means for reading the serial number of the patch. If the serial number read by the controller corresponds to a serial number programmed into the microprocessor of the controller, the controller determines that the patch and controller are compatible and will provide current to transdermally drive the medicament into the body of the patient.

The serial number may be formed by an integrated chip embedded in the patch. Additionally, the microprocessor in the controller may poll the patch serial number and compare it to a look-up table in the microprocessor for patch compatibility. If the patch is determined to be incompatible, no current will be permitted to be applied to the patch by the controller.

The present invention is also directed to a method for ensuring proper iontophoretic drug using an iontophoretic device dosage including a patch containing a drug and a reusable controller, comprising the steps of:

electrically comparing an identification of the controller to an identification of the patch to determine compatibility of the controller with the patch and permitting current to flow from the controller to the patch if the identification of the controller is determined to be compatible with the identification of the patch.

A preferred embodiment of the iontophoretic device, as well as other embodiments, objects, features and advantages of this invention, will be apparent from the following detailed description of illustrative embodiments thereof, which is to be read in connection with the accompanying drawings.

BRIEF DESCRIPTION OF THE DRAWINGS

FIG. 1 is a perspective view of an iontophoretic patch and a reusable controller of the present invention shown prior to connection.

FIG. 2 is a perspective view of an iontophoretic patch and reusable controller of the present invention shown after connection.

FIG. 3 is a perspective view of the connected patch and controller folded over, as shown by the arrow in FIG. 2, supported on the skin of a patient.

DETAILED DESCRIPTION OF THE PREFERRED EMBODIMENT

Figure 4:
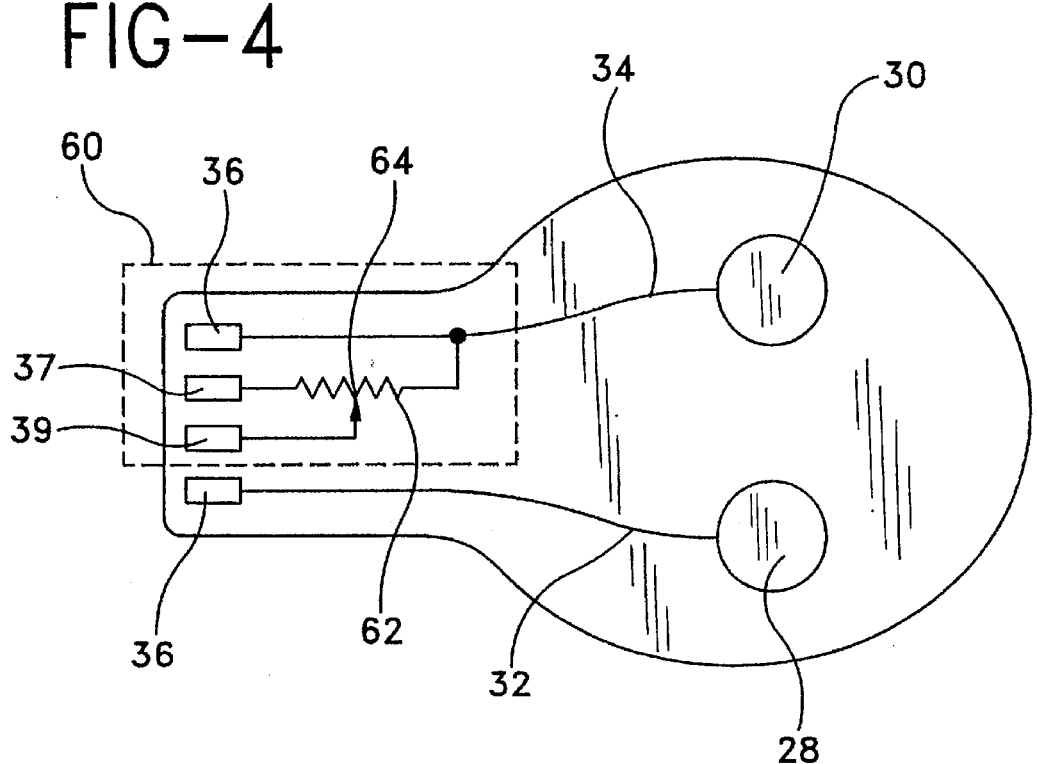
FIG. 4 is a schematic drawing of a patch illustrating a resistive network of the present invention.

Referring to FIGS. 1 and 2, an iontophoretic drug delivery device 10 including patch 12 and controller assembly 14 of the present invention is shown. Patch 12 is a generally planar flexible member formed of biocompatible material. Patch 12 may be formed of woven or non-woven textiles or polymers or may be any other construction well known in the art. Patch 12 is adhesively supported on the skin 16 of the patient (FIG. 3). Patch 12 includes an enlarged patch body 18 and an extending narrow tab 20. Patch body 18 includes opposed planar surfaces 22 and 24. Planar surface 24 is disposed for skin contact and includes a drug reservoir 26 (shown in phantom in FIG. 2) which contains an ionic drug typically in a gel form. While reservoir 26 is shown, any other known iontophoretic drug reservoir structure placing a drug in contact with the skin in an iontophoretic patch may be employed.

Skin contacting surface 24 further includes a pair of spaced apart electrodes 28 and 30. Each of electrodes 28 and 30 are positioned to be in contact with the skin once the patch 12 is secured, as shown in FIG. 3. The positioning of electrodes 28 and 30 is such that an electrical current path is established between electrodes 28 and 30 through the skin of the patient. Electrode 28 is also placed in conductive contact with reservoir 26 in a manner well-known in the iontophoretic delivery art. A direct current source may be connected between the electrodes 28 and 30 such that electrode 28 in contact with reservoir 26 assumes the same charge as the ionized drug contained in reservoir 26. Under the influence of electrical current passing from the electrode 28 to electrode 30 through the skin, the drug contained in reservoir 26 is transcutaneously delivered.

Referring to FIG. 4, electrical current is supplied from the controller 14 to electrodes 28 and 30 on the patch via electrical traces 32 and 34. Each of traces 32 and 34 may be one or more conductive paths extending from electrodes 28 and 30 to exposed conductive pads 36 positioned on a marginal edge of the patch tab 20. As described in further detail below, pads 36 are positioned for electrical connection to the controller 14, which provides a source of electrical current.

Referring back to FIG. 3, controller 14 houses electronic components 40 which supply the controlled application of electric current to electrodes 28 and 30. As is known in the art, electrical components 40 may include a source of electrical power such as a battery and additional electronic components, such as a microprocessor 44, used to send a controlled electrical current to electrodes 28 and 30.

As illustrated in FIG. 1 and 2, controller 14 includes a controller housing 42 which is generally rectangular in shape and includes an open front end 44 which accommodates tab 20 of patch 12. Housing 42 further accommodates a connection array 46 adjacent electronic components 40 (FIG. 3). Connection array 46 may include plural electrical terminals in electrical connection with electronic components 40 and which are connectable to pads 36 of tab 20. In the present illustrative embodiment, connection array 46 is an electrical connection device having plural spaced-apart, exposed conductive surfaces separated by an insulating material. It may be appreciated that any suitable electrical interconnection device may be employed in accordance with the present invention.

Housing 42 further includes a cover 48 which is used to close open front end 44 of housing 42. Cover 48 is slidably, captively retained on an upper wall 43 of housing 42. As shown in FIG. 1, cover 48 may be manually moved under thumb actuation to an open position exposing connection array 46 for electrical connection with pads 36 of tab 20. Cover 48 may be moved to a closed position shown in FIG. 2, covering connection array 46. With cover 48 in an open position patch 12 may be connected to controller 14.

In order to assure accurate alignment of pads 36 of tab 20 with the connection array 46 supported within housing 42, tab 20 is keyed to housing 42. Tab 20 includes an opening 50 which is designed to fit over an upwardly extending post 52. Opening 50 and post 52 are of similar shape so as to provide keyed accommodation of tab 20 and post 52. Post 52 extends upwardly from a bottom wall 45 of housing 42 adjacent the open front end 44 thereof. Post 52 is centrally located adjacent connection array 46 so as to accommodate tab 20 and positionally confine tab 20 within housing 44. The key structure included on both opening 50 and post 52 prevents incorrect positioning of patch 12 with respect to controller 14. In the present embodiment, both opening 50 and post 52 have a generally L-shaped cross section, however, any other mating shape which would prevent incorrect alignment may be employed.

Referring again to FIG. 2, patch 12 and controller 14 includes attachment means so as to permit the releasable support of controller 14 on patch 12 after interconnection between pads 36 and connective array 46 is established. Surface 22, which is opposed to skin-engaging surface 24 of patch 12, and the upper surface of housing wall 3 include cooperating fastening elements 55 and 56 thereon. In the present illustrative embodiment, the cooperative fastening elements include conventional hook and loop fasteners of the type sold under the trademark VELCRO. Any other cooperating type fasteners may be employed to achieve the same objective. One cooperating fastening element 55 is secured adhesively or otherwise to patch 12 on surface 22 while the other cooperating fastening member 56 is secured by adhesive or otherwise to the upper surface of wall 43 of housing 42. As described in further detail below, attachment of the mating hook and loop fasteners 55 or 56 provides for removable support of controller 14 on patch 12. It may be appreciated by those skilled in the art that the patch and controller may take any known form. The only requirement is that the patch be capable of being electrically connected to the controller.

Having described one embodiment of iontophoretic drug delivery device 10 of the present invention, its operation is described below.

Patch 12 may be adhesively secured to the skin 16 of the patient. Surface 24 of patch 12 is placed in intimate contact with the skin 16 so that electrodes 28 and 30 as well as drug containing reservoir 26 are supported in good intimate contact with the skin 16. In order to effect iontophoretic delivery of the drug from reservoir 26 transcutaneously through the skin 16, reusable controller 14 is electrically connected to patch 12. Housing 42 is slipped over extending tab 20 of patch 12 so that opening 50 in tab 20 is seated over upwardly extending post 52 of housing 42. Proper planar orientation is assured between patch 12 and controller 14 due to the key matability between opening 50 and post 52. As controller 14 is designed to be left in electrical connection with patch 12 during iontophoretic delivery of the drug contained in reservoir 16, controller 14 may be fastened to patch 12 so that it will be conveniently retained on the skin of the patient.

As shown in FIG. 2, once patch 12 is connected to controller 14, the controller may be flipped up in the direction of arrow A so that the mating hook and loop fasteners 55 and 56 engage each other to removably fasten controller 14 to patch 12 as shown in FIG. 3. The controller 14 is comfortably retained on the skin of the patient during iontophoretic drug delivery. At such time as a particular application of the drug is completed, the controller may be removed by separating the mating hook and loop fasteners 55 and 56. The controller may be disconnected and placed aside until the next administration of the drug is needed. The patch 12 may remain on the skin of the patient, eliminating the need for frequent replacement of the patch.

The iontophoretic drug delivery device of the present invention is specifically designed to ensure compatibility of the controller with the patch to which it is connected. This an important feature when utilizing a reusable controller to avoid supplying an incorrect amount of energy to the patch and possibly harm the patient. Different medicaments require different rates of delivery and dosage. Additionally, medicaments having lower pluralities or higher molecular weights require a higher current to be delivered through the skin. The controller may also be specifically programmed to deliver either an anionic drug or a cationic drug. Thus, compatibility of the controller to the patch is very important. Accordingly, in the present invention, the controller, patch or both includes a means for determining whether the controller is compatible with the patch. If it is determined that the patch and controller are incompatible, the controller prevents power from being supplied to the patch. In an alternative embodiment the controller, after identifying a particular patch, may reprogram itself to suit the particular patch characteristics.

Referring to FIG. 4, a patch including a resistive network 60 formed in accordance with the present invention is illustrated. In the preferred embodiment, the patch includes at least four connection tabs 35, 36, 37, 39. Two connection tabs 35, 36 are coupled via electrical traces or leads 32, 34 to the patch electrodes 28, 30. It is preferable that the electrical traces or leads 32, 34 be fabricated from a material having a low impedance. The resistive network 60 preferably comprises a resistor 62 which is preferably formed from an elongated resistive material which is tapped at a desired point along its length. The resistor 62 is coupled at one end to a connection tab 37 and its other end is coupled to electrical trace 34 which is in turn connected to the anode electrode of the patch. The tap 64 for the resistor 62 is coupled at its other end to a separate connection tab 39. The resistive network 60 of the patch provides a unique resistive ratio to the patch depending upon the location of the tap in the elongated resistive material.

Figure 5:
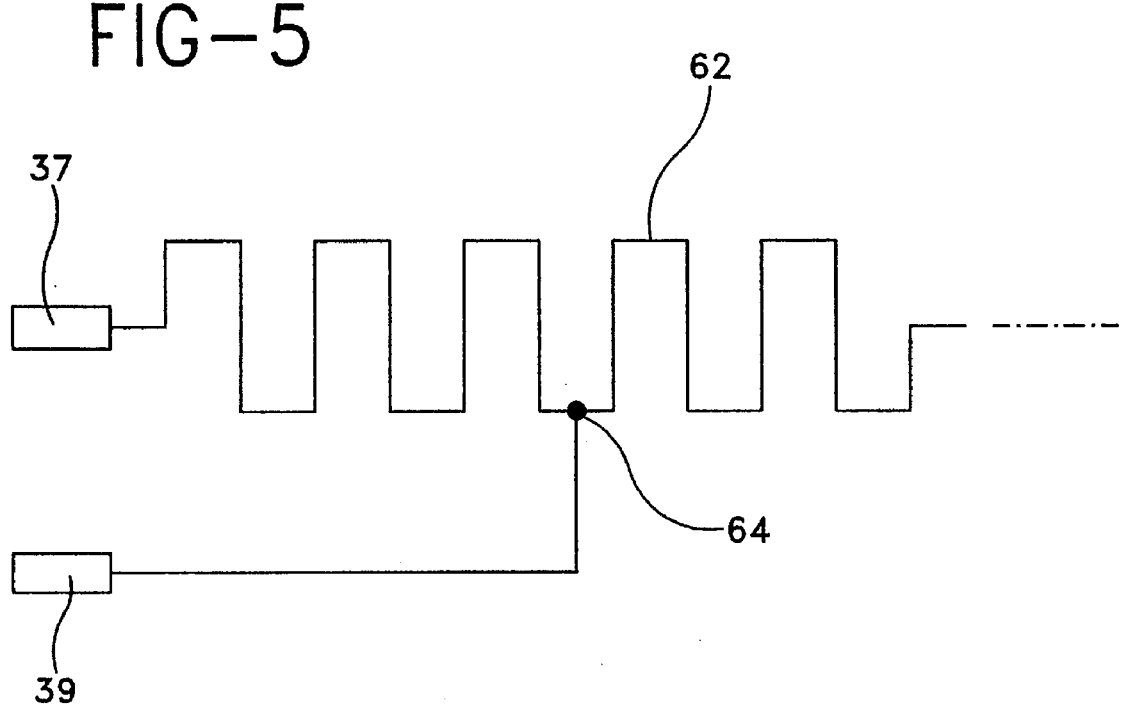
FIG. 5 is an illustration of a preferred patch resistive network of the present invention shown within the dashed outline (60) in FIG. 4.

The elongated resistive material forming patch resistor 62 may take any known form. For space constraints, the elongated conductive material may take on a serpentine shape, such as the square wave illustrated by FIG. 5, to increase the total resistance in the confined space available on the patch. Any periodically spaced "wave" may be conveniently tapped. The square wave shape and tapped "waves" will conveniently provide a visual indiction of the ratio of the resistances on opposite sides of the tap.

A common manufacturing process can be used to produce the patches, and the unique resistive ratio for the different patches is formed by tapping the different sections of the patch resistor 62. The resistor may be fabricated by silk screen printing or transfer process or by painting on the backing material of the patch. Preferably the electrical traces 32, 34 are fabricated from a silver ink or paint for best conductivity and the resistor is fabricated from a high impedance material such as carbon or graphite paint or ink. The paint or silver ink, for example, preferably is homogeneous in content and in cross-sectional area along its length to provide a constant resistance per unit length. In this way, it is assured that the ratio of the resistances on opposite sides of the tap is predictable irrespective of the total resistance of the elongated resistive material from which resistor 62 is formed.

One advantage of this manufacturing process is that the patch leads or conductors, including traces 32 and 34 may be formed at the same time and in the same manner as the resistance network 60. Both may be formed on the patch substrate by the silk screening or ink painting process. The leads and the resistors of the network may be formed from the same material. The leads connecting to the network may be of a relatively short length and a wide cross-section so that they have a low impedance, and the resistance network 60 may be formed with the elongated serpentine configuration described previously and with a relatively narrow cross-section for a relatively high impedance. As discussed below, the important value of the resistor network is not the absolute resistance, but rather the ratio of resistances that is created at the top connection tab. In one embodiment, a similar resistive network is formed in the controller electronics 40 located within the controller housing 42.

An important aspect of the preferred resistive networks formed in the patch and controller is that resistive ratios, rather than absolute values, determine compatibility of the patch and controller. It is envisioned that problems could arise in manufacturing and in application due to tolerances in the resistors being compared. For example, if the tolerance of the resistors permits a controller to supply power to an incompatible patch, the patient may be seriously harmed. In order to avoid the problems associated with absolute values, the preferred embodiment of the present invention uses resistive ratios formed by the resistive networks previously described.

When the patch is connected to the controller, the resistive network on the patch mates and electrically couples with the resistive network on the controller to form, together, a resistive bridge circuit. If the resistance ratios of the patch resistive network and controller resistive network, which define the bridge circuit, match, the differential voltage between the taps of the two networks will be substantially zero volts.

If the differential voltage is substantially equal to zero, the patch and controller are deemed to be compatible. If the differential voltage is anything other than approximately zero, the patch and controller are deemed incompatible. The differential voltage may be used in this case as a signal to the controller to instruct the controller not to deliver the drug to the patient.

Figure 6:
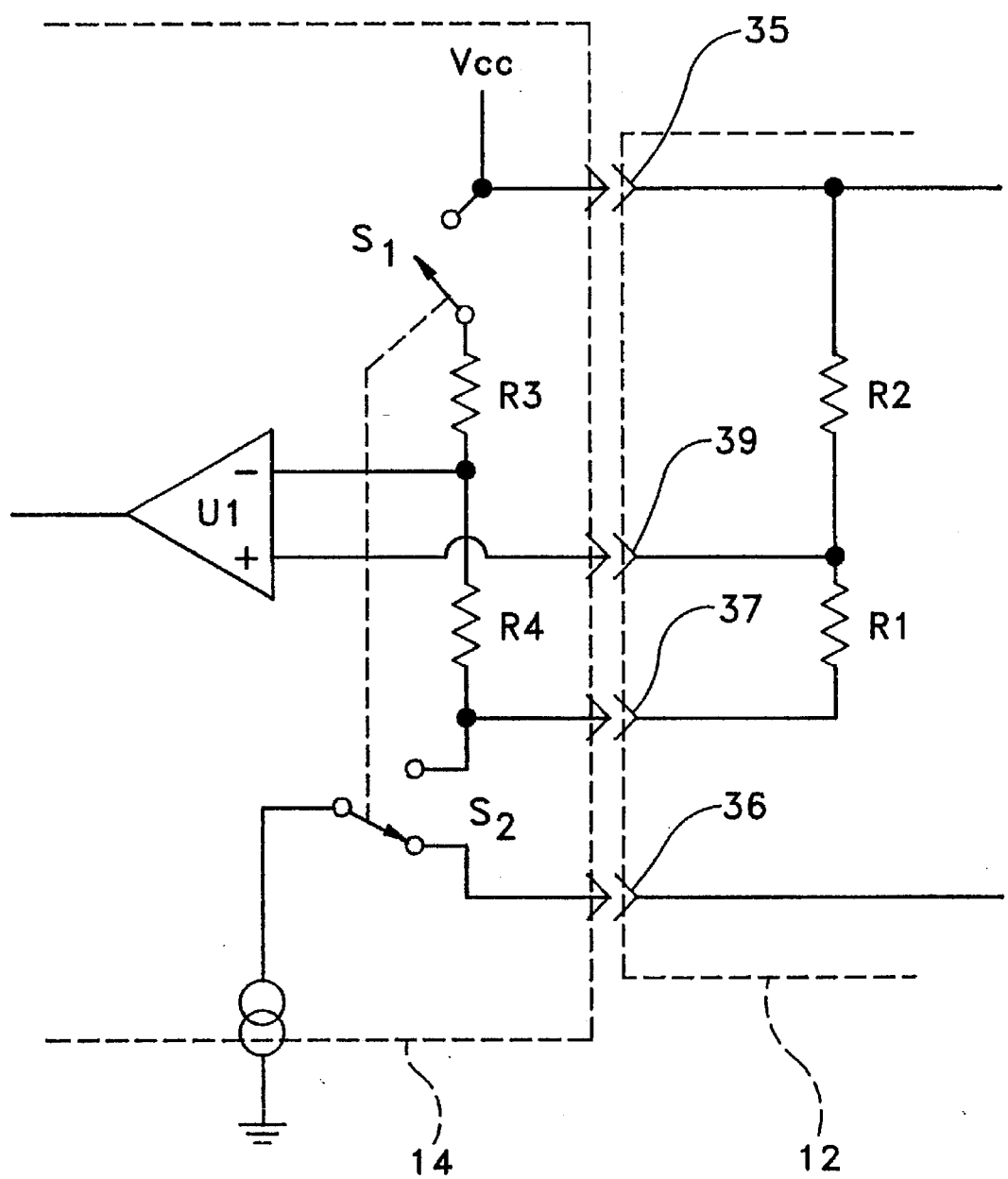
FIG. 6 is a circuit schematic of the controller resistive network coupled to the patch resistive network of the present invention.

Referring to FIG. 6, one embodiment of the compatibility determining means of the present invention is illustrated in a circuit schematic. The patch 12 is illustrated as including four connection tabs 35, 36, 37, 39. Two tabs 35, 36 are connected to the patch electrodes. Tab 39 is the tap in the patch resistive network separating the resistor 62 into resistors R1 and R2. The other end of a resistor R2 is electrically connected to tab 35 and the patch anode. The opposite end of resistor R1 is coupled to tab 37. Controller 14 includes a similar resistor network illustrated by resistors R3 and R4. The opposite end of resistor R3 from the tap is connected to switch S1 for selective coupling to the controller power source Vcc which is coupled to the patch anode at tab 35. The opposite end of resistor R4 is coupled to patch tab 37 and switch S2. The controller also includes a differential operational amplifier having its inverted input coupled to the tap into the R3, R4 resistor network. The non-inverting input is coupled to the connection tab 39 of the patch. The controller also includes switches S1 and S2 to selectively direct current through the resistor bridge circuit.

The resistor bridge identification means as illustrated in FIG. 6 works as follows: the current that would normally flow through the anode to the cathode is redirected by switch arrangement S1 and S2. The ratio of resistors R2 and R1 on the patch are compared to the ratio of resistors R3 and R4 on the controller. When the current is directed through the resistor bridge circuit by switches S1 and S2, the differential operational amplifier is used to measure the offset of the bridge. This value can be determined by a microprocessor or by a simple comparator. If the offset is determined to be non-zero, the controller is deemed incompatible with the patch and will not operate.

In an alternative embodiment, the current passing through the patch resistive network is measured by the controller electronics to determine a specific patch identification. The controller preferably includes a microprocessor to measure the voltage drop across each resistor of the resistive network of the patch and determine the ratio of the resistances comprising the network, and compare that ratio with a predetermined value stored in the microprocessor's memory. If the microprocessor determines that the measured voltage drop across the patch resistive network is compatible with the controller, the controller applies the proper current for the proper amount of time to treat the patient. Otherwise, if the patch and controller are deemed incompatible, the controller is disabled and no current is permitted to flow to the patch. The controller may also include means for indicating incompatibility with a patch such as a visual or audio indicator, e.g. an LED or an electronic buzzer, which may also be controlled by the microprocessor of the controller.

Figure 7:
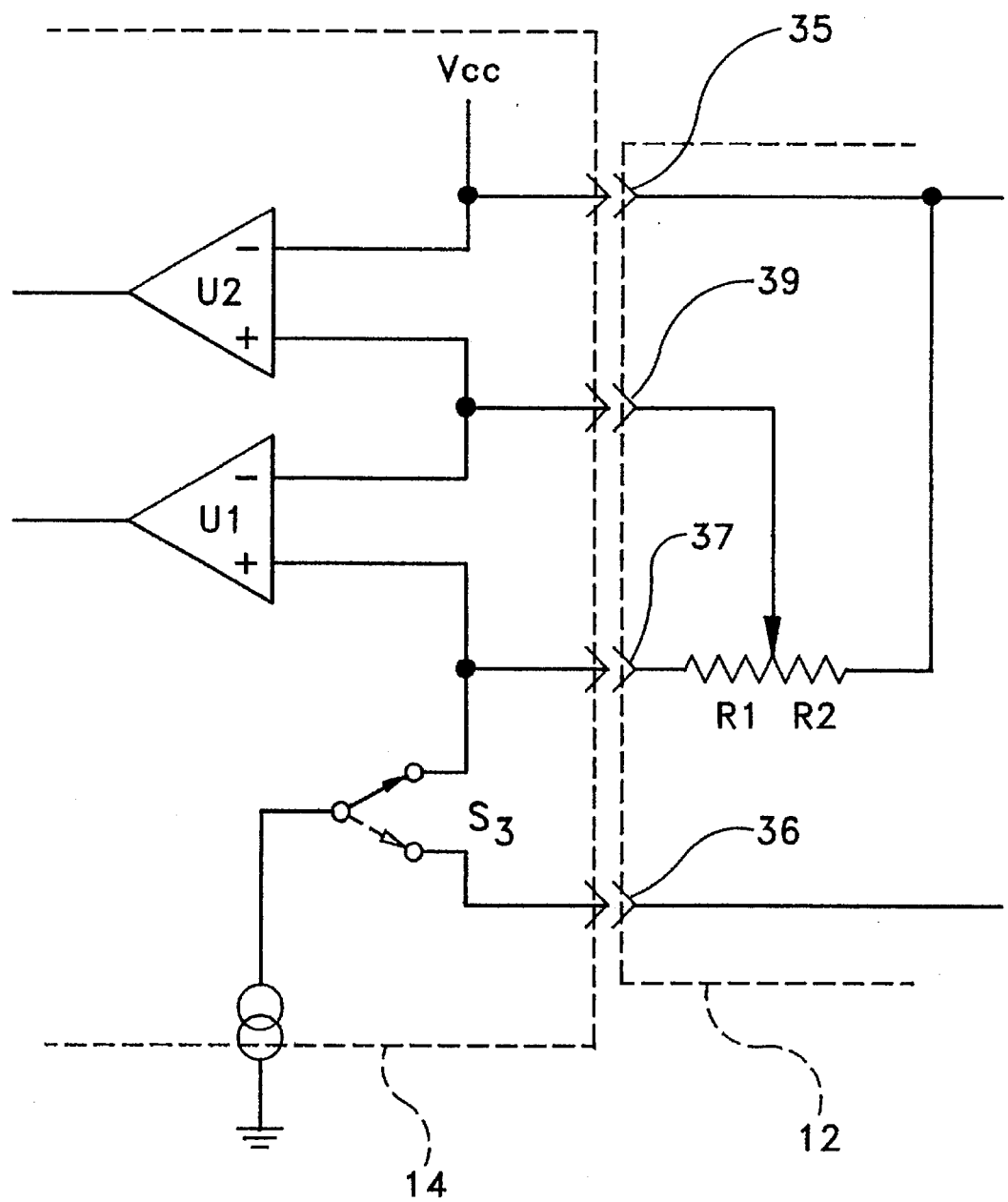
FIG. 7 is an alternative circuit schematic of the controller circuit and patch circuit to ensure compatibility according to the present invention.

The embodiment described above is schematically illustrated in FIG. 7. In FIG. 7, the patch configuration remains the same as that illustrated in FIG. 6; however, the controller electronics are slightly different. The controller includes four connection tabs to electrically connect the controller to the patch. The controller includes two differential operational amplifiers U2 and U3. A non-inverting input of U2 and an inverting input of U3 are coupled to the resistor network tap at tab 39. The non-inverting input of U3 is connected to the resistor network at tab 37. The inverting input of U2 is connected to the patch anode tab 3S as well as the controller power source Vcc. The controller includes switch S3 to direct the flow of current either through the resistors R1 and R2 of the patch resistor network or through the patch anode and cathode. The two differential operational amplifiers are used to measure the voltage drop across resistors R1 and R2 resulting in VR1 and VR2. The patch identification can be measured as the voltage VR2 divided by the voltage VR1 by a microprocessor having A/D converters. Based upon the patch identification, the compatibility of the patch and controller can be determined.

In yet another embodiment, the patch and controller identification may be in the form of an electronic serial number on the patch and means for reading the serial number in the controller. If the serial number is determined by the controller electronics to be a compatible patch, current is supplied to the patch. The serial number is preferably in the form of an integrated chip embedded in the patch. The controller is capable of being electrically coupled to the patch to read the serial number. The controller includes a microprocessor such that the controller may poll the patch to determine if the serial number is found in a look-up table in the microprocessor. If the serial number is not compatible with the particular controller, the controller will not be able to supply energy to the patch.

The present invention is also directed to the method of ensuring compatibility of a reusable controller with a patch to which it is connected. The method includes the steps of electrically comparing an identification of the patch and an identification of the controller to determine compatibility of the patch and controller and permitting current to flow from the controller to the patch only if the patch and controller are determined to have compatible identifications. Accordingly, the present invention provides an important safety feature of iontophoretic drug delivery devices which utilize reusable controllers.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

I claim:

1. An iontophoretic drug delivery device comprising:

a reusable controller having a power source;

a patch for attaching to the skin of a patient, the patch including electrodes in the form of an anode and a cathode, one of the said anode and said cathode including a reservoir containing an ionizable substance for transcutaneous delivery to the patient, said patch being removably, electrically connectable to said controller for delivering current from the controller to the patch electrodes; and means for determining whether the controller is compatible with the patch, the determining means including means for preventing current from the controller from being delivered to said patch electrodes when th epatch is connected to the controller if said controller and patch are deemed incompatible.

2. An iontophoretic drug delivery device as defined in claim 1, wherein the determining means comprises a resistor network in said controller and a resistor network in said patch, said controller including means for comparing resistive ratios of said controller and patch networks.

3. An iontophoretic drug delivery device as defined in claim 2, wherein said current delivery prevention means includes means for disabling said controller when the resistive ratios of said controller and said patch are determined to be incompatible.

4. An iontophoretic drug delivery device as defined in claim 3, wherein the comparing means comprises a microprocessor.

5. An iontophoretic drug delivery device as defined in claim 3, wherein the disabling means comprises a microprocessor.

6. An iontophoretic drug delivery device as defined in claim 2, wherein said patch resistor network comprises a resistor having a plurality of taps for creating a specific resistive ratio.

7. An iontophoretic drug delivery device as defined in claim 6, wherein said patch resistor comprises an elongated resistor formed from carbon.

8. An iontophoretic drug delivery device as defined in claim 1, wherein the determining means comprises a serial number located on said patch, and said controller includes means for reading said serial number.

9. An iontophoretic drug delivery device as defined in claim 8, wherein the serial number comprises an integrated circuit embedded in said patch.

10. An iontophoretic drug delivery device as defined in claim 9, wherein said reading means comprises a microprocessor in said controller which polls said patch serial number and compares the serial number to a look-up table in the microprocessor for compatibility.

11. An iontophoretic drug delivery device as defined in claim 1, wherein the determining means comprises a resistor network in said patch and means for measuring and calculating a voltage drop across said patch resistor bridge located in said controller to determine a patch identification.

12. An iontophoretic drug delivery device as defined in claim 11, wherein the means for measuring and calculating said voltage drop comprises a pair of differential operation amplifiers having inputs coupled to said resistor bridge and a microprocessor electrically connected to the outputs of said differential amplifiers.

13. An iontophoretic drug delivery device comprising:

a controller for providing a specific current to drive an ionizable substance into the skin of a patient, said controller including a resistive network;

a patch removably, electrically coupled to said controller, said patch including an anode and a cathode, one of said anode and cathode including a reservoir containing an ionizable substance; and electrically conductive lead coupled to the cathode and an electrically conductive lead coupled to said anode; and a resistive bridge coupled to said cathode lead; and means for comparing a resistive ratio of said controller resistive network with a resistive ratio of said patch bridge circuit, the controller including a means for disabling said controller which will permit current to flow from the controller to the patch only if the resistive ratio of said controller and said resistive ratio of said patch are deemed compatible.

14. An iontophoretic drug delivery device as defined in claim 13, wherein said comparing means comprises a microprocessor in said controller.

15. An iontophoretic drug delivery device as defined in claim 13, wherein said cathode lead and said resistive network applied to said path are selected from the group consisting of conductive metal, ink and paint.

16. An iontophoretic drug delivery device as defined in claim 15, wherein said cathode lead comprises silver.

17. An iontophoretic drug delivery device as defined in claim 15, wherein said resistive network comprises a resistive portion formed from carbon.

\* \* \* \* \*